US007519142B2

(12) United States Patent
Morita

(10) Patent No.: US 7,519,142 B2
(45) Date of Patent: Apr. 14, 2009

(54) RADIOGRAPHIC APPARATUS

(75) Inventor: Hisanori Morita, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 301 days.

(21) Appl. No.: 11/011,187

(22) Filed: Dec. 15, 2004

(65) Prior Publication Data

US 2005/0129168 A1 Jun. 16, 2005

(30) Foreign Application Priority Data

Dec. 16, 2003 (JP) .............................. 2003-418259

(51) Int. Cl.
*A61B 6/03* (2006.01)
(52) U.S. Cl. .......................................... 378/4; 378/901
(58) Field of Classification Search ...................... 378/4, 378/205, 210, 901; 345/424
See application file for complete search history.

(56) References Cited

U.S. PATENT DOCUMENTS

| 4,887,211 A * | 12/1989 | Thiel et al. .................. 382/131 |
| 5,566,220 A | 10/1996 | Saito et al. |
| 2003/0052879 A1 * | 3/2003 | Barth et al. .................. 345/424 |
| 2005/0151736 A1 * | 7/2005 | Schlegel et al. ............. 345/424 |

FOREIGN PATENT DOCUMENTS

| JP | 2002-078704 A | 3/2002 |
| JP | 2002-267622 A1 | 9/2002 |

OTHER PUBLICATIONS

Karolczak et al., Implementation of a cone-beam reconstruction algorithm for the single-circle source orbit with embedded misalignment correction using homogeneous coordinates, Medical Physics, vol. 28, Issue 10, pp. 2050-2069, Oct. 2001.*
Mitschke et al., Recovering the X-ray Projection Geometry for Three-dimensional tomographic reconstruction with additional sensors: Attached camera versus external navigation system, Medical Image Analysis, vol. 7, Issue 1, pp. 65-78, Mar. 2003.*
Kornmesser et al., Fast Feldkamp-reconstruction for real-time reconstruction using C-arm systems, 2002, Proceedings of the 16th International Congress and Exposition Computer Assisted Radiology and Surgery (CARS 2002), ISBN 3-540-43655-3, pp. 430-434.*

* cited by examiner

Primary Examiner—Chih-Cheng G Kao
Assistant Examiner—John M Corbett
(74) Attorney, Agent, or Firm—Cheng Law Group PLLC

(57) ABSTRACT

A reconstruction process for processing pixel data for tomographic volume image data uses a concise reconstruction algorithm based on an assumption that an axis of X-ray emission axis always exists on a plane orthogonal to an axis of revolution of an X-ray tube and an FPD. In time of the reconstruction process, a corrected parameter is applied to the reconstruction algorithm for correcting a mechanical displacement occurring between the axis of revolution of the X-ray tube and FPD and the axis of X-ray emission. Thus, errors due to the mechanical displacement may be avoided by a simple data processing of setting the corrected parameter to the reconstruction algorithm, without impairing lightness of a data processing load on the reconstruction algorithm.

5 Claims, 7 Drawing Sheets

RADIOGRAPHIC APPARATUS

BACKGROUND OF THE INVENTION (1). Field of the Invention

This invention relates to a radiographic apparatus having a radiation emitting device for emitting radiation in a cone-shaped beam and a two-dimensional radiation detecting device for detecting transmitted radiation images. The radiation emitting device and radiation detecting device are revolvable about an axis of revolution provided by a straight line extending through an object under examination, for scanning a site of interest of the object. Pixel data for sectional images are put to a reconstruction process based on radiation image detection data outputted from the radiation detecting device in response to an emission of radiation in the cone-shaped beam, and on a reconstruction algorithm. More particularly, the invention relates to a technique for reducing a data processing load resulting from a mechanical displacement occurring between the axis of revolution of the radiation emitting device and radiation detecting device and an axis of radiation emission.

(2). Description of the Related Art

Conventional radiographic apparatus of the type noted above include a C-shaped arm driving X-ray radio-graphic apparatus. As shown in FIG. 1, a known C-shaped arm type X-ray radiographic apparatus includes an X-ray tube (radiation emitting device) 51 for emitting X rays in a cone-shaped beam and a two-dimensional X-ray detector (two-dimensional radiation detecting device) 52 (eg. a flat panel type detector) for detecting transmitted X-ray images. The X-ray tube 51 and X-ray detector 52 are mounted at one end and at the other end of a C-shaped arm 53 to be opposed to each other. When the C-shaped arm 53 is driven, the X-ray tube 51 and X-ray detector 52 are moved along two opposite arcuate tracks about a common center located in a patient M. Synchronously with a movement of X-ray tube 51 on one of the arcuate tracks, the X-ray detector 52 is moved on the other arcuate track while maintaining a fixed distance to the X-ray tube 51. In this way, radiography is performed to carry out an image reconstruction process for creating three-dimensional volume data of a region of interest of the patient M (hereinafter called simply "reconstruction process").

In the image reconstruction process, the X-ray tube 51 and X-ray detector 52 are driven to acquire data from the site of interest of the patient M in each scan position. These data, after a filtering process, are back-projected to predetermined lattice points of a three-dimensional lattice virtually set to the region of interest of the patient M, thereby generating three-dimensional volume data of the region of interest (see, for example, Japanese Unexamined Patent Publication No. 2002-267622, pages 7 and 8, and FIGS. 9 and 10).

However, the conventional X-ray radiographic apparatus has a problem of an excessive data processing load resulting from a mechanical displacement occurring between an axis of revolution RA of X-ray tube 51 and X-ray detector 52 and an axis of radiation emission XA.

In the conventional apparatus, an algorithm for the reconstruction process is simplified by assuming that the axis of X-ray emission XA always exists on a single plane orthogonal to the axis of revolution RA. However, a mechanical displacement could occur between the axis of X-ray emission XA and the axis of revolution RA, whereby the axis of X-ray emission XA deviates from and inclines relative to the plane on which it should exist.

Assuming that the axis of X-ray emission XA is not inclined relative to the plane, as shown in FIG. 2, only one surface of a three-dimensional lattice point matrix V set to the site of interest is visible when seen from the X-ray tube 51. On the other hand, when the axis of X-ray emission XA is inclined relative to the plane, as shown in FIG. 3, two surfaces of the three-dimensional lattice point matrix V are visible. Specifically, when a reconstruction process is carried out, assuming the state shown in FIG. 2 although the actual state is as shown in FIG. 3, a displacement will occur between each lattice point J in the lattice point matrix V and a corresponding detection point K on the X-ray detecting plane of the X-ray detector 52. The reconstruction process carried out based on X-ray image pixel data acquired in this state of displacement will result in errors due to the inclination of the axis of X-ray emission XA.

As a result, artifacts will appear in a final X-ray sectional image.

In order to perform a proper reconstruction process even when the axis of X-ray emission XA is inclined relative to the axis of revolution RA as described above, a different, sophisticated algorithm for reconstruction is used which incorporates complicated computing steps to cope with the inclination of the axis of X-ray emission XA. Alternatively, a reconstruction process is carried out by performing a data conversion according to an amount of inclination of the axis of X-ray emission XA for all of the X-ray image detection data outputted from the X-ray detector 52.

In such cases, however, the sophisticated algorithm incorporating complicated computing steps, or the data conversion performed beforehand for all of the X-ray image detection data, inevitably results in a sharp increase in the load of data processing.

Where the above algorithm is used, X-ray image detection data collected with the detection point K inclined relative to the direction of arrangement because of the displacement between the lattice point J and the detection point K on the X-ray detector as shown in FIG. 3 is not stored as data continuous along a row or column from each lattice point J as shown in FIG. 2. Instead, the data is stored as data arranged intermittently, skipping the row or column of the detection point K. Therefore, the X-ray image detection data stored intermittently is read intermittently little by little. This results in an inconvenience of not enabling an efficient calculating process to be performed by reading data to be used continuously at a time and temporarily storing the data in a cache memory providing a high-speed data transfer.

SUMMARY OF THE INVENTION

This invention has been made having regard to the state of the art noted above, and its object is to provide a radiographic apparatus for reducing a data processing load added as a result of a mechanical displacement occurring between an axis of revolution of a radiation emitting device and a three-dimensional radiation detecting device and an axis of radiation emission.

The above object is fulfilled, according to this invention, by a radiographic apparatus comprising a radiation emitting device for emitting radiation in a cone-shaped beam to a site of interest of an object under examination, a two-dimensional radiation detecting device for detecting transmitted radiation images of the object resulting from the radiation emitted in the cone-shaped beam, an image pickup system scanning device for scanning the site of interest by revolving the radiation emitting device and the two-dimensional radiation detecting device about an axis of revolution provided by a straight line extending through the object while maintaining the radiation emitting device and the two-dimensional radiation detecting device opposed to each other across the object, and a reconstruction processing device for performing, based on radiation image detection data outputted from the two-dimensional radiation detecting device in response to the radiation emitted in the cone-shaped beam, and on a reconstruction algorithm, an image reconstruction process using pixel data for tomographic volume image data on a lattice point matrix virtually set to the site of interest, the reconstruction algorithm used by the reconstruction processing device being characterized in that:

(A) an axis of radiation emission is assumed to exist constantly on a plane orthogonal to the axis of revolution of the radiation emitting device and the two-dimensional radiation detecting device; and (B) a parameter applied to the reconstruction algorithm in time of the reconstruction process by the reconstruction processing device is a corrected parameter for correcting a mechanical displacement occurring between the axis of revolution of the radiation emitting device and the two-dimensional radiation detecting device and the axis of radiation emission.

The radiographic apparatus according to this invention, when performing radiography, scans the site of interest of the object by causing the radiation image pickup system scanning device to revolve the radiation emitting device for emitting radiation in a cone-shaped beam and the two-dimensional radiation detecting device for detecting transmitted radiation images, about the straight line extending through the object while maintaining the radiation emitting device and the two-dimensional radiation detecting device opposed to each other across the site of interest. At the same time, the reconstruction processing device performs, based on radiation image detection data outputted from the two-dimensional radiation detecting device in response to the radiation emitted in the cone-shaped beam, and on the reconstruction algorithm, an image reconstruction process using pixel data for tomographic volume image data on the lattice point matrix virtually set to the site of interest.

In time of the reconstruction process of the pixel data for radiation tomographic volume image data, the reconstruction processing device uses the reconstruction algorithm on the assumption that the axis of radiation emission is assumed to exist constantly on the plane orthogonal to the axis of revolution of the radiation emitting device and the two-dimensional radiation detecting device. That is, when the reconstruction processing device performs the reconstruction process, the corrected parameter is applied to the reconstruction algorithm for correcting a mechanical displacement occurring between the axis of revolution of the radiation emitting device and the two-dimensional radiation detecting device and the axis of radiation emission.

Thus, the reconstruction processing device performs the following process as the reconstruction process for processing the pixel data for radiation tomographic volume image data. A concise reconstruction algorithm (with a light data processing load) is used on the assumption that the axis of radiation emission always exists on the plane orthogonal to the axis of revolution of the radiation emitting device and the two-dimensional radiation detecting device. At the same time, a construction is provided for applying the corrected parameter to the reconstruction algorithm, in time of the reconstruction process performed by the reconstruction processing device, for correcting a mechanical displacement occurring between the axis of revolution of the radiation emitting device and the two-dimensional radiation detecting device and the axis of radiation emission. Thus, errors due to the mechanical displacement occurring between the axis of revolution of the radiation emitting device and the two-dimensional radiation detecting device and the axis of radiation emission may be avoided by a simple data processing for applying the corrected parameter to the reconstruction algorithm. That is, a high-speed data processing is realized without impairing the lightness of the data processing load on the reconstruction algorithm.

This invention provides the following construction in order to fulfill such an object.

The radiographic apparatus according to this invention further comprises:

a measuring device for measuring a mechanical displacement of the axis of radiation emission;

a parameter calculating device for calculating a corrected parameter corrected according to an amount of mechanical displacement measured by the measuring device; and a parameter storage device for storing the corrected parameter calculated by the parameter calculating device;

wherein the reconstruction processing device performs the reconstruction process by using tomographic volume image data of the object acquired by the radiation emitting device, the two-dimensional radiation detecting device and the image pickup system scanning device, and the corrected parameter stored in the parameter storage device.

With this construction, the apparatus itself can carry out the series of processes from measuring the mechanical displacement between the axis of revolution of the radiation emitting device and two-dimensional radiation detecting device and the axis of radiation emission to storing the corrected parameter.

The reconstruction algorithm uses, as the corrected parameter calculated by the parameter calculating device, a plane-related inclination correcting parameter for correcting a mechanical displacement caused by the axis of radiation emission inclined relative to the plane orthogonal to the axis of revolution.

Preferably, this plane-related inclination correcting parameter is obtained as follows:

(C1) set a first radiation emission axis on an assumption that the axis of radiation emission always exists on the orthogonal plane;

(C2) determine beforehand an amount of inclination of a second radiation emission axis including an inclination relative to the first radiation emission axis in time of actual measurement;

(C3) assume further that the radiation emitting device exists on the first radiation emission axis, and set a third radiation emission axis by taking into account the amount of inclination determined; and (C4) determine distances of shifting from the first radiation emission axis to the third radiation emission axis of a set position of the lattice point matrix virtually set to the site of interest and a position of a radiation detecting plane of the two-dimensional radiation detecting device.

This construction sets to the reconstruction algorithm the plane-related inclination correcting parameter for correcting a mechanical displacement caused by the axis of radiation emission inclined relative to the plane orthogonal to the axis of revolution. As a result, errors of data processing results due to the mechanical displacement in which the axis of radiation emission is inclined relative to a rectangular plane are appropriately avoided.

The plane-related inclination correcting parameter is obtained based on the distances of shifting from the first radiation emission axis to the third radiation emission axis of the set position of the lattice point matrix virtually set to the site of interest and the position of the radiation detecting plane of the two-dimensional radiation detecting device. As a result, the plane-related inclination correcting parameter is obtained easily by a simple processing of changing the set position of the lattice point matrix and the position of the radiation detecting plane of the two-dimensional radiation detecting device.

Preferably, the reconstruction algorithm is characterized in that:

(D) a radiation detecting plane of the two-dimensional radiation detecting device is assumed to be orthogonal to the axis of radiation emission at all times; and (E) simultaneously with (D) above, the radiation detecting plane is assumed to be orthogonal to the axis of radiation emission when obtaining a plane-related inclination correcting parameter, and a direction of shifting to a position of the radiation detecting plane is set parallel to the radiation detecting plane.

With this construction, the reconstruction algorithm is based on the further assumption that the radiation detecting plane of the two-dimensional radiation detecting device is constantly orthogonal to the axis of radiation emission. This promotes the conciseness of the reconstruction algorithm. As a result, the data processing load of the reconstruction process becomes lighter.

The radiation detecting plane of the two-dimensional radiation detecting device is shifted only in a direction parallel to the radiation detector plane. This simplifies the process of shifting the radiation detector plane in time of obtaining the plane-related inclination correcting parameter. Thus, the plane-related inclination correcting parameter is obtained with increased ease.

In the radiographic apparatus according to this invention, it is preferred that the radiation emitting device and the two-dimensional radiation detecting device are mounted at one end and at the other end of an arm to be opposed to each other, the image pickup system scanning device driving the arm to revolve the radiation emitting device and the two-dimensional radiation detecting device, thereby scanning the site of interest. For example, the radiation emitting device and the two-dimensional radiation detecting device may be mounted at opposite ends of a C-shaped arm to be opposed to each other.

Further, in the radiographic apparatus according to this invention, the image pickup system scanning device may be arranged to revolve the radiation emitting device and the two-dimensional radiation detecting device so that the radiation includes at least 180°+ a spread angle of the cone-shaped beam around the object.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

An embodiment of this invention will be described hereinafter with reference to the drawings.

Figure 1:
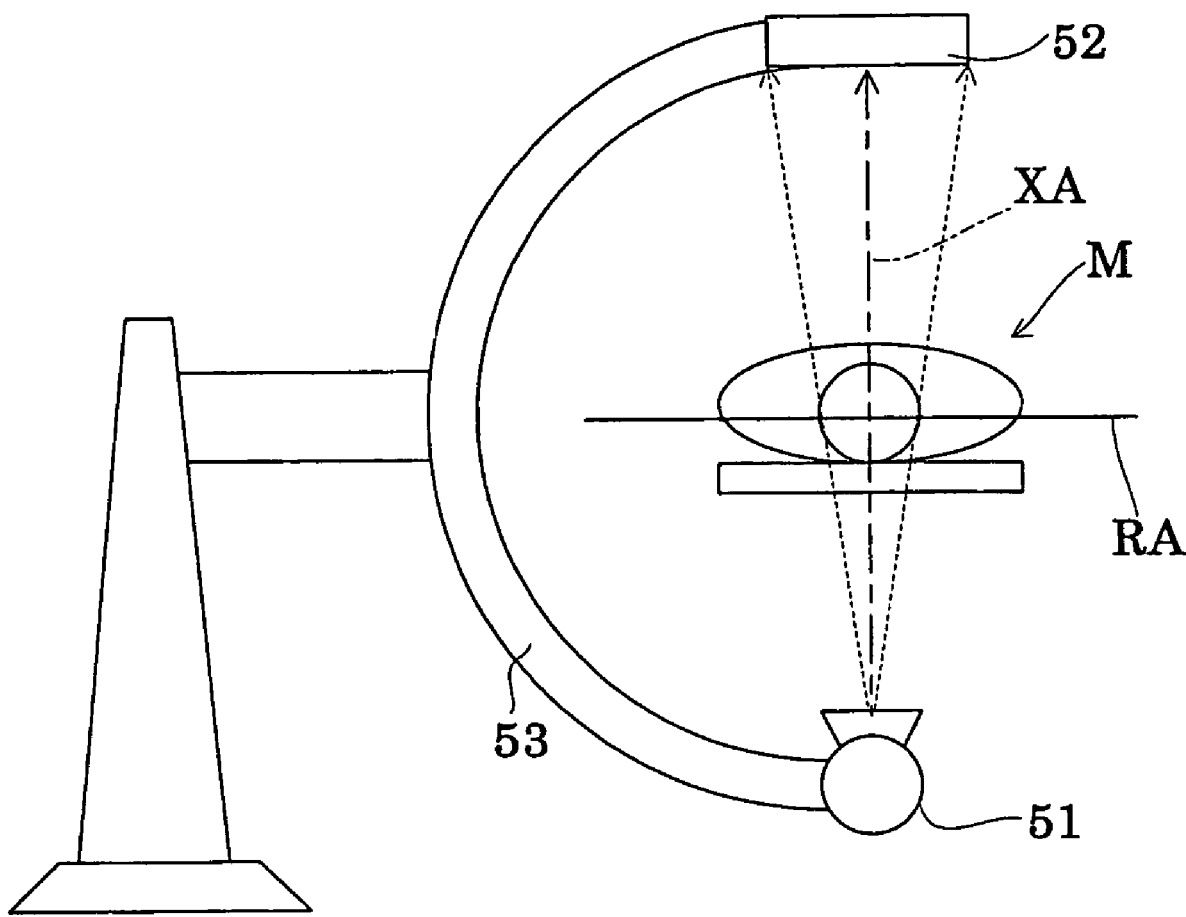
FIG. 1 is a schematic view showing an outline of an X-ray image pickup system of a conventional apparatus.
Figure 2:
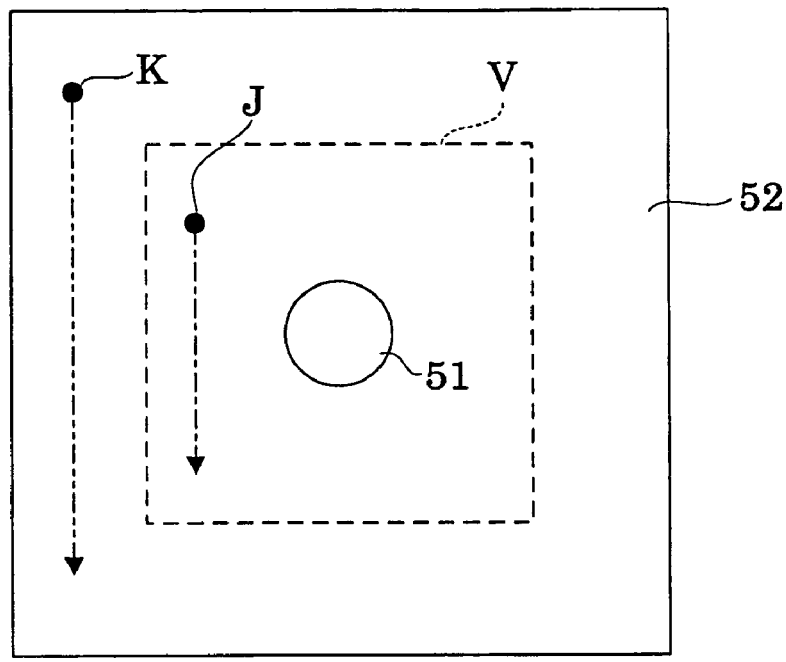
FIG. 2 is a schematic view showing a state of no mechanical displacement between an axis of revolution of an X-ray tube and an FPD and an axis of X-ray emission in the conventional apparatus.
Figure 3:
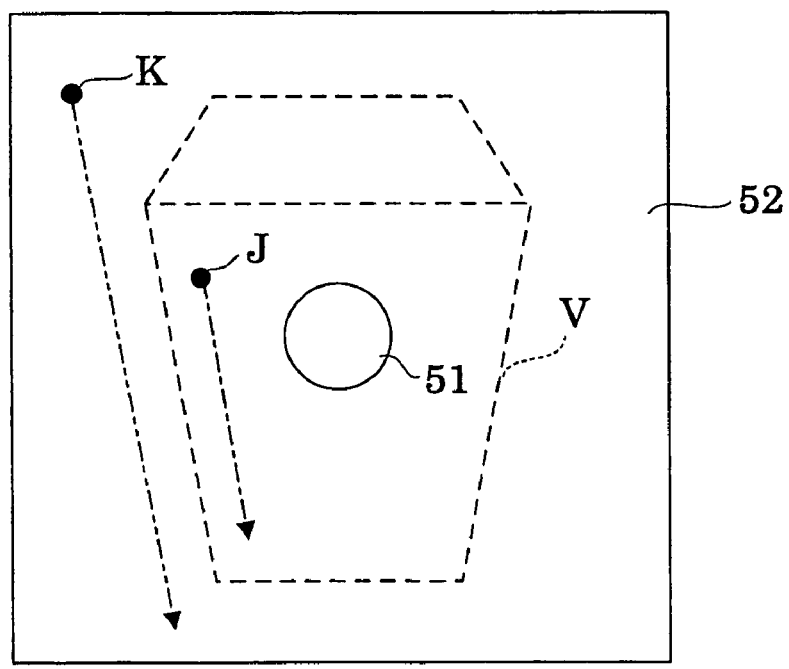
FIG. 3 is a schematic view showing a state of a mechanical displacement occurring between the axis of revolution of the X-ray tube and FPD and the axis of X-ray emission in the conventional apparatus.
Figure 4:
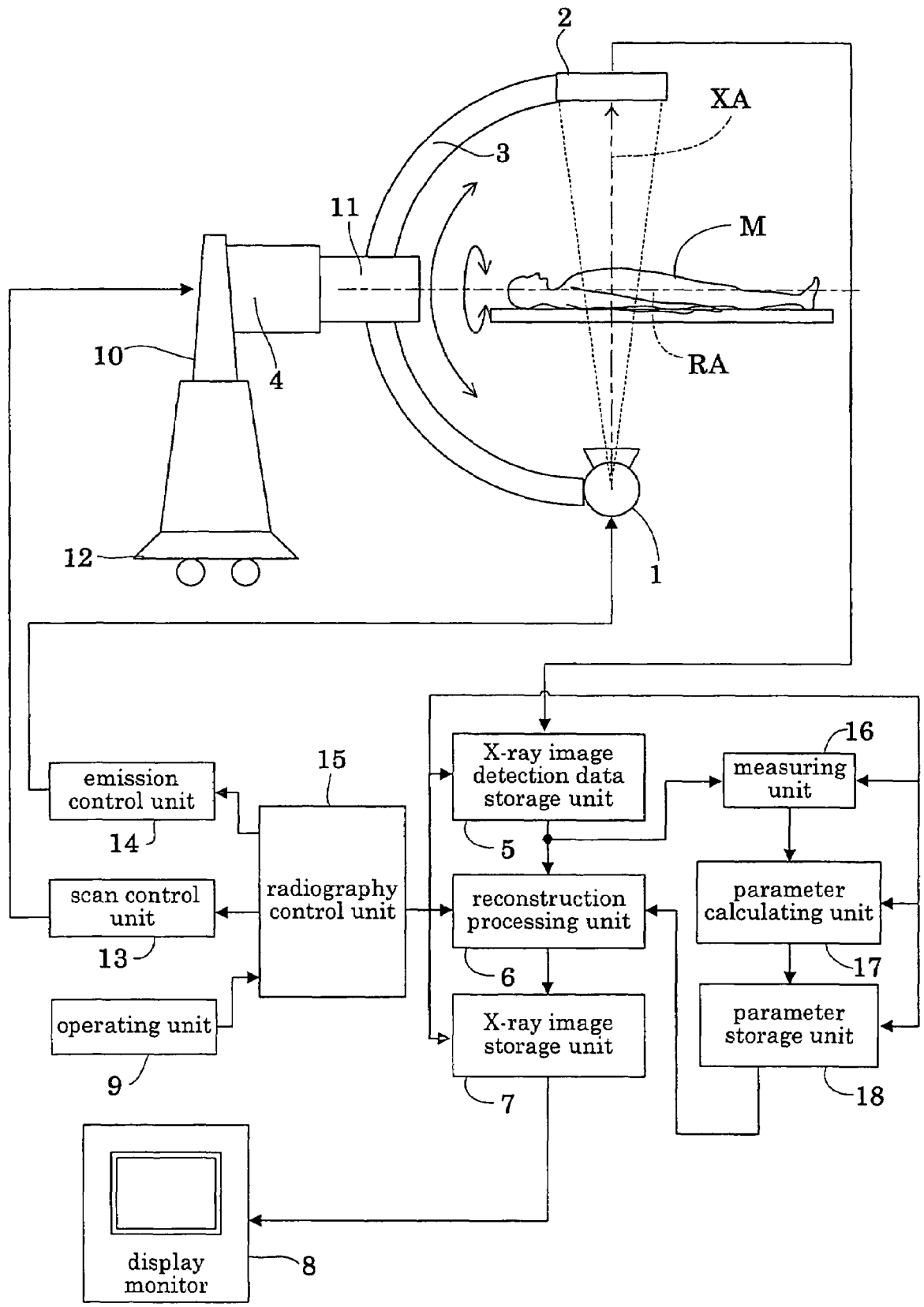
FIG. 4 is a block diagram showing an overall construction of an X-ray radiographic apparatus according to this invention.
Figure 5:
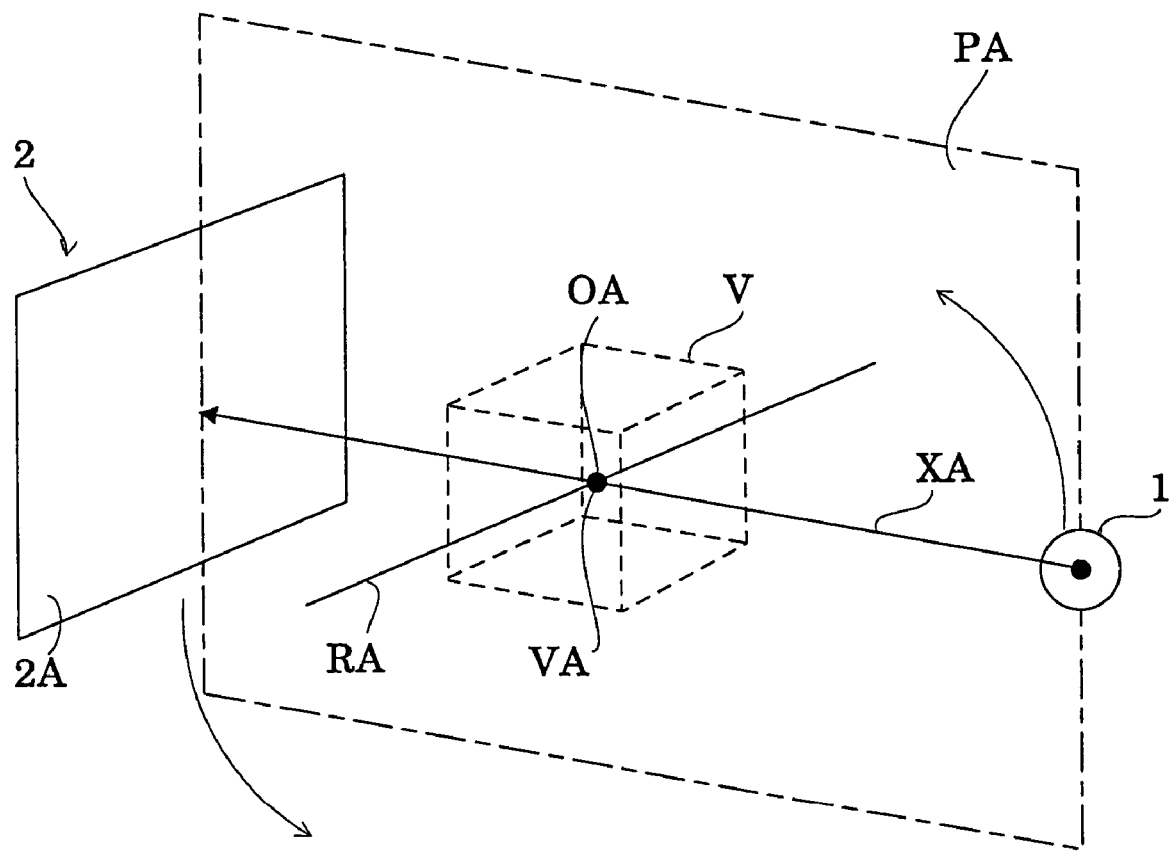
FIG. 5 is a schematic view showing, in perspective, a mechanical arrangement of an X-ray image pickup system in the apparatus according to this invention.

The apparatus in this embodiment is a C-shaped arm driving X-ray radiographic apparatus of the type that emits X rays in a cone-shaped beam, which is used in a medical institution such as a hospital. FIG. 4 is a block diagram showing an overall construction of the X-ray radiographic apparatus (hereinafter called simply "radiographic apparatus"). FIG. 5 is a schematic view showing a mechanical arrangement of an X-ray image pickup system in the apparatus according to this invention. The X-ray radiographic apparatus corresponds to the radiographic apparatus of this invention.

As shown in FIG. 4, the radiographic apparatus in this embodiment includes an X-ray tube 1 for emitting X rays in a cone-shaped beam, a flat panel type X-ray detector 2 (hereinafter called "FPD 2" where appropriate) for detecting transmitted X-ray images. The X-ray tube 1 and X-ray detector 2 are mounted at one end and at the other end of a C-shaped arm 3 to be opposed to each other. The C-shaped arm 3 is driven by an X-ray image pickup system scanning mechanism 4 to revolve the X-ray tube 1 and FPD 2 about an axis of revolution RA provided by a straight line extending through a patient M, while maintaining the X-ray tube 1 and FPD 2 opposed to each other across a site of interest of patient M, thereby to scan the site of interest of patient M. The apparatus further includes an X-ray image detection data storage unit 5 for storing X-ray image detection data outputted from the FPD 2 as X rays are emitted in the cone-shaped beam, a reconstruction processing unit 6 for performing, based on the X-ray image detection data stored in the detection data storage unit 5 and a reconstruction algorithm, a reconstruction of pixel data for tomographic volume image data on a lattice point matrix virtually set to the site of interest, an X-ray image storage unit 7 for storing the pixel data for tomographic volume image data reconstructed by the reconstruction processing unit 6, a display monitor 8 for displaying the tomographic volume image data, and an operating unit 9 for inputting instructions and data required for radiography.

The X-ray tube 1 corresponds to the radiation emitting device of this invention. The flat panel type X-ray detector 2 corresponds to the two-dimensional radiation detecting device. The X-ray image pickup system scanning mechanism 4 corresponds to the image pickup system scanning device. The reconstruction processing unit 6 corresponds to the reconstruction processing device.

The C-shaped arm 3 is received in and supported by a forward end of a cylindrical member 11 attached in horizontal posture to an upper portion of a support column 10. The cylindrical member 11 is attached to be rotatable about a central axis thereof. With rotation of the cylindrical member 11, the C-shaped arm 3 is rotatable about the axis RA coinciding with the central axis of the cylindrical member 11. The C-shaped arm 3 is supported by the cylindrical member 11 to be rotatable while sliding along the curve in the longitudinal direction of the arm. The support column 10 is vertically movably erected on a mobile base 12. With movement of the mobile base 12 or vertical movement of the support column 10, the X-ray tube 1 and FPD 2 along with the C-shaped arm 3 make a horizontal translation.

In the case of the radiographic apparatus in this embodiment, therefore, the movement of the mobile base 12 or vertical movement of the support column 10 can change the position of the straight line extending through the patient M and serving as the axis of revolution RA of the X-ray tube 1 and FPD 2, and thus change a radio graphing position.

The X-ray image pickup system scanning mechanism 4, under control of an scan control unit 13, selectively causes scanning action of the X-ray image pickup system by rotation of the C-shaped arm 3 about the axis RA, and scanning action of the X-ray image pickup system by sliding of the C-shaped arm 3 relative to the cylindrical member 11. In scanning action of the X-ray image pickup system in this embodiment, the X-ray tube 1 and FPD 2 are revolved through a range of an approximately half circle (180°+ a spread angle of the cone-shaped beam) around the patient M. However, the X-ray tube 1 and FPD 2 may be revolved through a range of one complete circle (360° or more) around the patient M.

The X-ray image pickup system scanning mechanism 4 is constructed by combining a rotating mechanism including an electric motor and rotary gears and a moving mechanism such as a rack and pinion.

The apparatus in this embodiment performs X-ray radiography as follows. First, the X-ray tube 1 and FPD 2 revolve around the patient M as described above, whereby the X-ray image pickup system scans the site of interest. At this time, the X-ray tube 1 emits X rays in a cone-shaped beam to the site of interest of patient M under control of an emission control unit 14. At the same time, X-ray image detection data outputted from the FPD 2 in response to the X-ray emission in a cone-shaped beam is stored in the X-ray image detection data storage unit 5.

The reconstruction processing unit 6 performs, based on the X-ray image detection data stored in the detection data storage unit 5 and the reconstruction algorithm, a reconstruction of pixel data for tomographic volume image data on the lattice point matrix virtually set to the site of interest. The pixel data for tomographic volume image data reproduced by the reconstruction processing unit 6 is stored in the X-ray image data storage unit 7.

The lattice point matrix set to the site of interest in time of the reconstruction process by the reconstruction processing unit 6 includes not only a three-dimension lattice point matrix but may include a two-dimensional lattice point matrix as appropriate. When the three-dimensional lattice point matrix is set, three-dimension volume data is obtained. When the two-dimensional lattice point matrix is set, two-dimensional plane data is obtained. A specific example of the reconstruction algorithm used by the reconstruction processing unit 6 is the well-known Feldkamp reconstruction algorithm for a cone-shaped beam. However, the reconstruction algorithm used by the reconstruction processing unit 6 is not limited to the Feldkamp reconstruction algorithm for a cone-shaped beam.

The pixel data for tomographic volume image data stored in the X-ray image data storage unit 7 may be displayed on the screen of the display monitor 8 at any time as two-dimensional or three-dimensional tomographic volume image data of the site of interest. The data may be outputted as X-ray photographs printed on printing paper from an image output device (not shown), or as electrophotographs stored on storage media such as compact disks.

A radiography control unit 15 includes a CPU and an operating program for performing an overall control of the apparatus. Specifically, the control unit 15 transmits command signals and data to various components such as the scan control unit 13 and radiation control unit 14, in accordance with progress of radiography and in response to inputs to the operating unit 9.

The radiographic apparatus in this embodiment is constructed for reducing a data processing load added by a mechanical displacement occurring between the axis of revolution of the X-ray tube 1 and FPD 2 and the axis of X-ray emission. This aspect will particularly be described hereinafter.

In this embodiment, the reconstruction algorithm used by the reconstruction processing unit 6, as shown in FIG. 5, assumes that the axis of X-ray emission XA always exists on a single plane (hereinafter called "the rectangular plane" as appropriate) PA orthogonal to the axis of revolution RA of the X-ray tube 1 and FPD 2. A parameter applied to the reconstruction algorithm in time of a reconstruction process performed by the reconstruction processing unit 6 is a corrected parameter for correcting a mechanical displacement occurring between the axis of revolution RA of the X-ray tube 1 and FPD 2 and the axis of X-ray emission XA.

In this way, the algorithm is simplified by assuming that the axis of X-ray emission XA always exists on the rectangular plane PA. As shown in an alternate long and short dash line in FIG. 6, a mechanical displacement may occur between the axis of X-ray emission XA and axis of revolution RA, whereby the axis of X-ray emission XA is inclined relative to the rectangular plane PA (shown in FIG. 5). In this case, a point on the X-ray detecting plane 2A of FPD 2 corresponding to each lattice point Q in the lattice point matrix V is displaced from detecting point H to detecting point h. A reconstruction process carried out in this state would result in errors due to the inclination of the axis of X-ray emission XA relative to the rectangular plane PA. That is, the data processing would result in an inconvenience of artifacts appearing in a final tomographic volume image data.

In order to avoid such an inconvenience, the apparatus in this embodiment sets beforehand a corrected parameter to the reconstruction algorithm for correcting a mechanical displacement occurring between the axis of revolution RA of the X-ray tube 1 and FPD 2 and the axis of X-ray emission XA in time of a reconstruction process by the reconstruction processing unit 6.

Specifically, the apparatus includes a measuring unit 16 for measuring a mechanical displacement occurring between the axis of revolution RA of the X-ray tube 1 and FPD 2 and the axis of X-ray emission XA, a parameter calculating unit 17 for calculating a corrected parameter incorporating a correction according to an amount of mechanical displacement measured by the measuring unit 16, and a parameter storage unit 18 for storing the corrected parameter calculated by the parameter calculation unit 17.

The measuring unit 16 corresponds to the measuring device of this invention. The parameter calculating unit 17 corresponds to the parameter calculating device. The parameter storage unit 18 corresponds to the parameter storage device.

The construction of each component will particularly be described hereinafter with reference to the block diagram of FIG. 4 and the flow chart shown in FIG. 8.

The measuring unit 16 sets a phantom (imitation patient) for measurement (step S1), collects X-ray image detection data (step S2), and determines a mechanical displacement between the axis of revolution RA of the X-ray tube 1 and FPD 2 and the axis of X-ray emission XA based on the X-ray image detection data (step S3).

The parameter calculating unit 17 calculates a corrected parameter incorporating a correction according to an amount of mechanical displacement measured by the measuring unit 16 (step S4). Specifically, the corrected parameter used is a plane-related inclination correcting parameter for correcting a mechanical displacement caused by the axis of X-ray emission XA inclined relative to the rectangular plane PA. In obtaining this plane-related inclination correcting parameter, instead of assuming that the axis of X-ray emission XA (first radiation emission axis) always exists on the rectangular plane PA and that the X-ray detecting plane 2A of FPD 2 is always orthogonal to the axis X-ray emission XA, it is assumed, as shown in FIG. 7, the position of the lattice point matrix V virtually set to the site of interest and the position of the X-ray detecting plane 2A of FPD 2 have shifted by distances (shift distances) L1 and L2 corresponding to the amount of inclination of the axis of X-ray emission XA" (third radiation emission axis).

Figure 6:
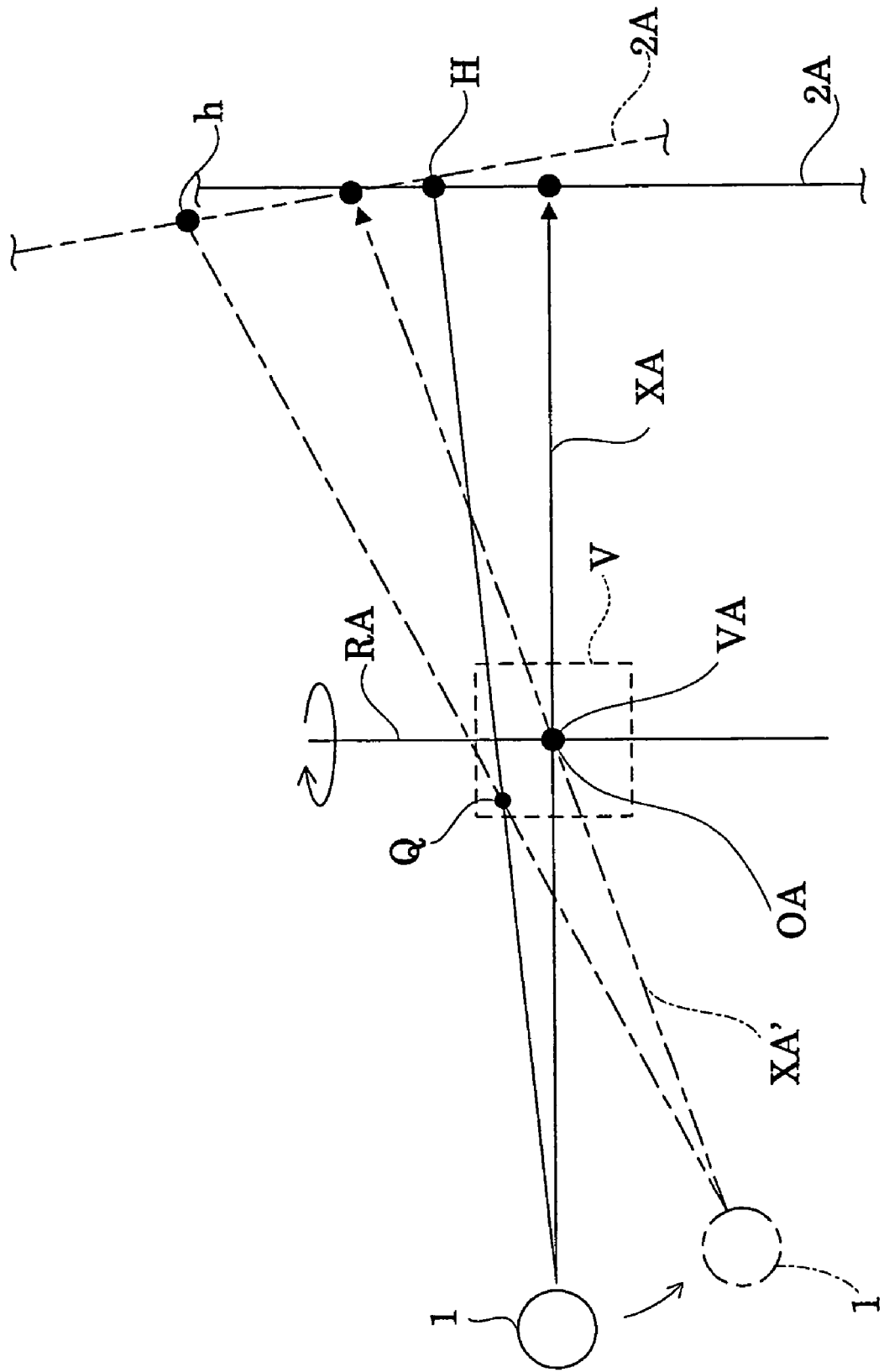
FIG. 6 is a schematic view showing a state of a mechanical displacement occurring between the axis of revolution of the X-ray tube and FPD and the axis of X-ray emission in the apparatus according to this invention.
Figure 7:
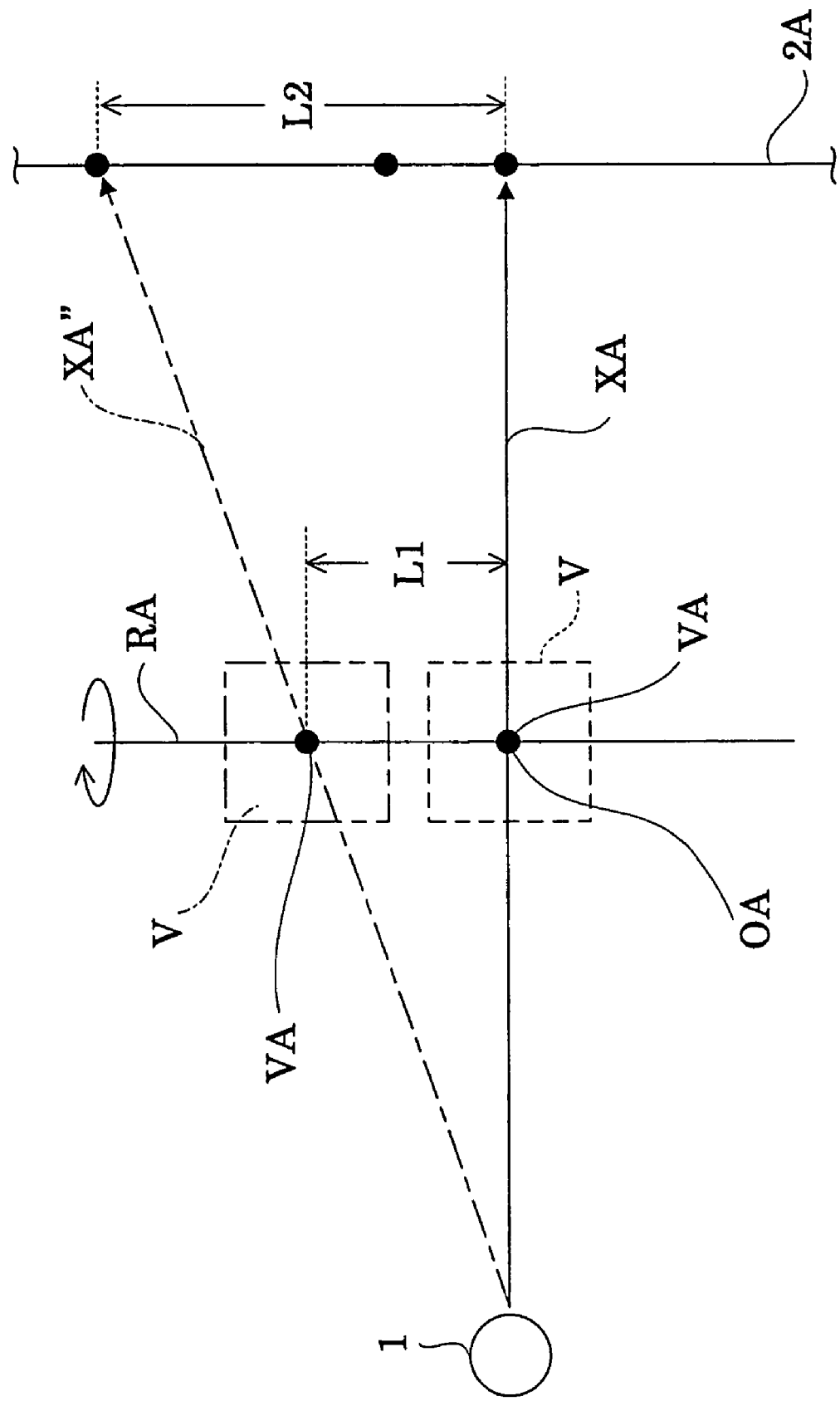
FIG. 7 is a schematic view showing shifts of a lattice point matrix and an X-ray detecting plane of the FPD in time of obtaining a corrected parameter in the apparatus according to this invention.

That is, the positions of the X-ray tube 1, FPD 2 and lattice point matrix V, shown in FIG. 6, in the state where the axis of X-ray emission XA' (second radiation emission axis) is inclined relative to the rectangular plane PA, are translated in the direction parallel to the X-ray detecting plane 2A (in the direction in which the axis of revolution RA extends) until the inclination of the X-ray tube 1 is compensated for as shown in FIG. 7. The plane-related inclination correcting parameter is determined by regarding the distance L1 the lattice point matrix V has moved as a distance to the axis of X-ray emission XA" (third radiation emission axis) to which the lattice point matrix V has shifted according to the amount of inclination of the axis of X-ray emission XA' (second radiation emission axis), and regarding the distance L2 the FPD 2 has moved as a distance the FPD 2 has shifted according to the amount of inclination of the axis of X-ray emission XA.

Figure 8:
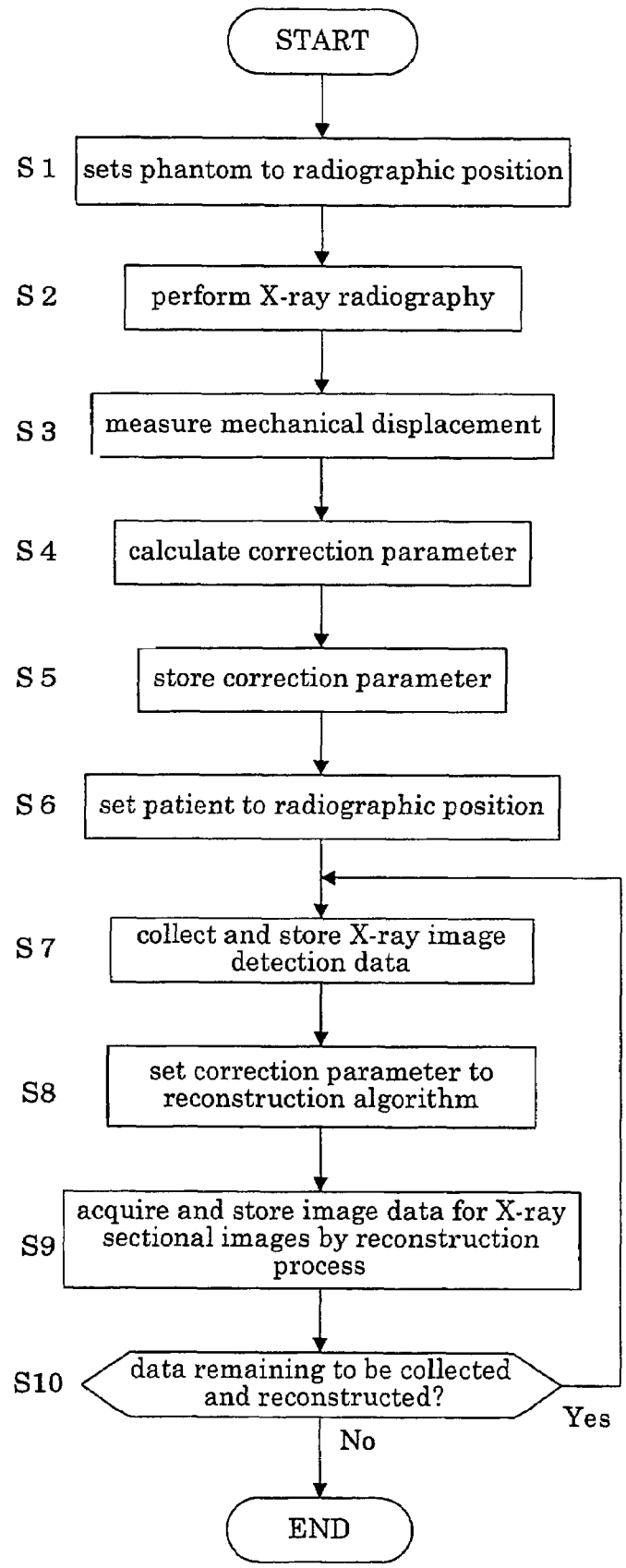
FIG. 8 is a flow chart showing an X-ray radiographic process performed by the apparatus according to this invention.

Reverting to FIGS. 4 and 8, the parameter storage unit 18 stores the corrected parameter calculated by the parameter calculating unit 17 (Step S5).

The radiography control unit 15 transmits command signals and data also to the mechanical displacement measuring unit 16, parameter calculating unit 17 and parameter storage unit 18 in accordance with progress of radiography and in response to inputs to the operating unit 9.

In the above construction, when the processes in steps S1 through S5 are completed, the patient to be examined is set to the radiographic position (step S6). Radiography is started to collect and store X-ray image detection data of the patient (Step S7).

The reconstruction processing unit 6, when performing a reconstruction process, apply the corrected parameter stored in the parameter storage unit 18 to the reconstruction algorithm (step S8). Data processing is carried out based on the corrected parameter and reconstruction algorithm set. Pixel data for tomographic volume image data is thereby acquired and stored in the X-ray image data storage unit 7 (step S9).

When the collection and reconstruction process of the pixel data for tomographic volume image data are completed (step S10), the series of processes will be ended.

The reconstruction processing unit 6, measuring unit 16, parameter calculating unit 17 and parameter storage unit 18 are formed of a CPU, operating program, memory and so on. Data is transferred between the CPU and memory through a cache memory, not shown, included in the CPU and capable of high-speed data transfer.

With the above construction, even when a mechanical displacement occurs between the axis of revolution RA of the X-ray tube 1 and FPD 2 and the axis of X-ray emission XA, errors in data processing results may be avoided by the simple process of applying a corrected parameter to the reconstruction algorithm, without impairing the lightness of the data processing load on the reconstruction algorithm.

The X-ray radiographic apparatus in this embodiment is the C-shaped arm driving type which is particularly prone to a mechanical displacement between the axis of revolution RA of the X-ray tube 1 and FPD 2 and the axis of X-ray emission XA. However, the described construction is effective to reduce the data processing load added by the mechanical displacement between the axis of revolution RA of the X-ray tube 1 and FPD 2 and the axis of X-ray emission XA.

In the apparatus in this embodiment, the reconstruction algorithm is based on the assumption that, as shown in FIG. 5, the X-ray detecting plane 2A of FPD 2 is always orthogonal to the axis of X-ray emission XA (i.e. parallel to the axis of revolution RA). This promotes the conciseness of the reconstruction algorithm and the lightness of the data processing load. Data processing results of the reconstruction process hardly change even when the X-ray detecting plane 2A of FPD 2 somewhat deviates from the state of being orthogonal to the axis of X-ray emission XA. That is, images outputted to the display monitor are substantially the same as those resulting from a data processing based on a complicated algorithm, which are clear images free from artifacts.

With the reconstruction algorithm based on the assumption that the X-ray detecting plane 2A of FPD 2 is always orthogonal to the axis of X-ray emission XA, X-ray image detection data is collected in a state of being aligned continuously to the detection points on the FPD 2. Consequently, continuous data may be stored in the cache memory at a time. An efficient processing may be carried out while performing a high-speed data transfer between the cache memory and CPU.

The plane-related inclination correcting parameter is obtained by regarding the set position of the lattice point matrix V and position of the X-ray detector plane 2A of FPD 2 as having shifted the distances corresponding to the inclination of the axis of X-ray emission XA relative to the rectangular plane PA. Thus, the plane-related inclination correcting parameter may be obtained easily by a simple process of changing the set position of the lattice point matrix V and position of the X-ray detector plane 2A of FPD 2. The apparatus in this embodiment requires only moving of the setting position of the lattice point matrix V and position of the X-ray detector plane 2A along the X-ray detector plane 2A (in the direction in which the axis of revolution RA extends). The process of the position shifting is simple, and involves hardly any additional processing load.

In the apparatus in this embodiment, as shown in FIG. 5, the lattice point matrix V is set such that the center VA of the matrix coincides with an intersection OA of the axis of revolution RA of the X-ray tube 1 and FPD 2 and the axis of X-ray emission XA. As a result, the axis of revolution RA of the X-ray tube 1 and FPD 2 and the axis of X-ray emission XA are maintained to extend through the center VA of the lattice point matrix V during a scanning operation of the X-ray tube 1 and FPD 2. This feature further promotes the conciseness of the reconstruction algorithm and the lightness of the data processing load.

A mechanical displacement of the axis of X-ray emission XA on the rectangular plane PA is equivalent to the scanning operation of the X-ray tube 1 and FPD 2 having progressed by an extent corresponding to the mechanical displacement of the axis of X-ray emission XA. A corrected parameter incorporating a correction corresponding to the mechanical displacement of the axis of X-ray emission XA on the rectangular plane PA may be obtained in substantially the same way as a non-corrected parameter.

This invention is not limited to the above embodiment, but may be modified as follows:

(1) The apparatus described above is constructed to detect transmitted X-ray images with the FPD 2. In one example of modifications, the apparatus may have the same construction as in the described embodiment except that, in place of the FPD 2, an image intensifier is used to detect transmitted X-ray images.

(2) In the apparatus in the described embodiment, the C-shaped arm 3 is mounted on the mobile base 12 to be movable with the base 12. This invention is applicable also to a C-shaped arm movably attached to a ceiling and a floor-mounted C-shaped arm.

(3) The described apparatus is the C-shaped arm driving type. This invention is applicable also to an apparatus of the type that drives an arm other than the C-shaped arm, and to an apparatus of the non-arm drive type in which the X-ray tube 1 and FPD 2 are not mounted on a single arm.

(4) While the described apparatus is a medical apparatus, this invention is applicable also to an apparatus for use in industry or for atomic power.

(5) While the described apparatus uses X rays as radiation, this invention is applicable also to an apparatus using radiation other than X rays.

This invention may be embodied in other specific forms without departing from the spirit or essential attributes thereof and, accordingly, reference should be made to the appended claims, rather than to the foregoing specification, as indicating the scope of the invention.

What is claimed is:

1. A radiographic apparatus comprising:
   radiation emitting means for emitting radiation in a cone-shaped beam to a site of interest of an object under examination;
   two-dimensional radiation detecting means for detecting transmitted radiation images of the object resulting from the radiation emitted in the cone-shaped beam;
   image pickup system scanning means for scanning the site of interest by revolving said radiation emitting means and said two-dimensional radiation detecting means about an axis of revolution provided by a straight line extending through the object while maintaining said radiation emitting means and said two-dimensional radiation detecting means opposed to each other across the object; and
   reconstruction processing means for performing, based on an X-ray image detection data storage unit for storing radiation image detection data outputted from said two-dimensional radiation detecting means in response to the radiation emitted in the cone-shaped beam as data in a state of being continuously aligned with respect to the direction of arrangement of detection points, and on a reconstruction algorithm, an image reconstruction process on a lattice point matrix virtually set to the site of interest, said reconstruction algorithm used by said reconstruction processing means being characterized in that:
   (A) an axis of radiation emission is assumed to exist constantly on a plane orthogonal to the axis of revolution of said radiation emitting means and said two-dimensional radiation detecting means such that when the reconstruction processing is performed, X-ray image detection data is sequentially read from said X-ray image detection data storage unit in a state of being aligned continuously to the detection points; and
   (B) a parameter set to said reconstruction algorithm at time of the reconstruction process by said reconstruction processing means is a parameter using a plane-related correcting parameter for correcting a mechanical displacement such that the axis of radiation emission is relatively inclined to a plane orthogonal to the axis of revolution;
   said radiographic apparatus, further comprising:
   measuring means for measuring a mechanical displacement of the axis of radiation emission generated with respect to said radiation for said axis of revolution;
   parameter calculating means for calculating said plane-related correcting parameter corrected according to an amount of mechanical displacement measured by said measuring means; and
   parameter storage means for storing the corrected parameter calculated by said parameter calculating means;
   wherein said reconstruction processing means further has a cache memory for reading continuous radiation image detection data to be used at a time from the X-ray image data detection data storage unit and performs calculating process while temporarily storing the data in said cache memory, and
   wherein said parameter calculating means obtains said plane-related inclination correcting parameter as follows:
   (C1) set a first radiation emission axis on an assumption that the axis of radiation emission always exists on said orthogonal plane;
   (C2) determine beforehand an amount of inclination of a second radiation emission axis including an inclination relative to said first radiation emission axis at time of actual measurement;
   (C3) assume further that said radiation emission means exists on said first radiation emission axis, and set a third radiation emission axis by taking into account said amount of inclination determined; and
   (C4) determine distances of shifting from said first radiation emission axis to said third radiation emission axis of a set position of the lattice point matrix virtually set to the site of interest and a position of a radiation detecting plane of said two-dimensional radiation detecting means.

2. A radiographic apparatus as defined in claim 1, wherein said reconstruction algorithm is characterized in that:
   (D) a radiation detecting plane of said two-dimensional radiation detecting means is assumed to be orthogonal to said axis of radiation emission at all times; and
   (E) simultaneously with (D) above, said radiation detecting plane is assumed to be orthogonal to said axis of radiation emission when obtaining a plane-related inclination correcting parameter, and a direction of shifting to a position of said radiation detecting plane is set parallel to said radiation detecting plane.

3. A radiographic apparatus as defined in claim 2, wherein said image pickup system scanning means is arranged to revolve said radiation emitting means and said two-dimensional radiation detecting means so that the radiation includes at least 180°+ a spread angle of the cone-shaped beam around said object.

4. A radiographic apparatus as defined in claim 1, wherein said radiation emitting means and said two-dimensional radiation detecting means are mounted at one end and at the other end of an arm to be opposed to each other, said image pickup system scanning means driving said arm to revolve said radiation emitting means and said two-dimensional radiation detecting means, thereby scanning said site of interest.

5. A radiographic apparatus as defined in claim 1, wherein said radiation emitting means and said two-dimensional radiation detecting means are mounted at opposite ends of a C-shaped arm to be opposed to each other.

* * * * *